(12) United States Patent
Hwang et al.

(10) Patent No.: US 9,862,961 B2
(45) Date of Patent: Jan. 9, 2018

(54) BIOMASS PRODUCTION INCREASING GENE AND TRANSGENIC PLANT USING SAME

(71) Applicant: POSTECH ACADEMY-INDUSTRY FOUNDATION, Gyeongsangbuk-do (KR)

(72) Inventors: Il Doo Hwang, Gyeongsangbuk-do (KR); Kang Min Kim, Gyeongsangbuk-do (KR); Hyun Suk Kim, Jeollabuk-do (KR)

(73) Assignee: POSTECH ACADEMY-INDUSTRY FOUNDATION (KR)

( * ) Notice: Subject to any disclaimer, the term of this patent is extended or adjusted under 35 U.S.C. 154(b) by 369 days.

(21) Appl. No.: 14/406,254

(22) PCT Filed: May 10, 2013

(86) PCT No.: PCT/KR2013/004186
§ 371 (c)(1),
(2) Date: Dec. 8, 2014

(87) PCT Pub. No.: WO2013/183864
PCT Pub. Date: Dec. 12, 2013

(65) Prior Publication Data
US 2015/0143585 A1    May 21, 2015

(30) Foreign Application Priority Data
Jun. 8, 2012 (KR) .................... 10-2012-0061613

(51) Int. Cl.
C12N 15/82 (2006.01)
C07K 14/415 (2006.01)

(52) U.S. Cl.
CPC ........ *C12N 15/8242* (2013.01); *C07K 14/415* (2013.01); *C12N 15/8261* (2013.01)

(58) Field of Classification Search
None
See application file for complete search history.

(56) References Cited

U.S. PATENT DOCUMENTS

| 2003/0024010 A1* | 1/2003 | Cahoon | A23D 9/00 800/281 |
| 2003/0172402 A1 | 9/2003 | Eriksson et al. | |
| 2006/0107345 A1* | 5/2006 | Alexandrov | C07K 14/415 800/278 |
| 2007/0092490 A1* | 4/2007 | Lee | C12N 15/86 424/93.2 |
| 2007/0238107 A1* | 10/2007 | Guo | C12N 15/1058 435/6.11 |
| 2013/0333068 A1* | 12/2013 | Coffin | C12N 15/8247 800/275 |

FOREIGN PATENT DOCUMENTS

| KR | 10-0833473 B1 | 5/2008 |
| KR | 10-2011-009993 A | 9/2011 |
| KR | 10-2012-0035019 A | 4/2012 |
| KR | 10-2012-0036757 A | 4/2012 |
| WO | WO 2009134339 A2 * | 11/2009 |

OTHER PUBLICATIONS

Tang et al (Dexamethasone-Inducible Green Fluorescent Protein Gene Expression in Transgenic Plant Cells. Geno. Prot. Bioinfo. vol. 2: 15-23, 2004).*
NCBI, GeneBank accession No. BAB 11345.1 (Feb. 14, 2004).
NCBI, GeneBank accession No. AA000836.1 (Dec. 20, 2002).

* cited by examiner

*Primary Examiner* — Medina A Ibrahim
*Assistant Examiner* — Wayne Zhong
(74) *Attorney, Agent, or Firm* — Riverside Law LLP

(57) ABSTRACT

The present disclosure relates to, inter alia, a gene for increasing biomass production isolated from *Arabidopsis thaliana*, and a method for producing a transgenic plant by using the same. More specifically, the present disclosure provides, inter alia, a composition for increasing production of plant biomass, a recombinant expression vector and a transgenic plant, comprising a base sequence encoding for the amino acid sequence of sequence number 2. Consequently, by using the gene for increasing biomass production of the present disclosure, it is possible to obtain a transgenic plant with which the amount of biomass production is increased and, ultimately, by using the same, it can be expected to be possible to increase starting materials for the pulp and papermaking industries, and starting materials for bioethanol.

7 Claims, 7 Drawing Sheets

SEQUENCE LISTING

<160> NUMBER OF SEQ ID NOS: 4

<210> SEQ ID NO 1
<211> LENGTH: 1245

```
<212> TYPE: DNA
<213> ORGANISM: Arabidopsis thaliana L. Heynh.

<400> SEQUENCE: 1
atgggatctg tatcgctgaa gattggcgat ggaaccgcaa gattcaagcg atcaacgctt     60
ttttcttcag ctatcaacct ccttatgctt ttctctatag tcactacaaa tctctttgca    120
ctatacgcct tctcgtctcg gtctcaatcc cacacgccac accctcttca ttccaacaat    180
gtctctttgg tttctcaaca tctctcactc atcctcagag aaatcgattc ctcccaccac    240
acactcactc agatggagaa acagattatt ggttatgaat ctctcgatct ctcgcaacaa    300
gaagttccac aagagcttaa acttttcctt caacaacatc agcttcctct tggtaaagat    360
tctcgtactg gtatcacaca aatggttgca tctgttggac attcctgtga aatgtctcta    420
gatttgttat ctcagtatat gtcgtataat gtctttgaaa aatgtcctga tgattggagc    480
ctagctcaga agttgattct ccgtgcttgt gaaccgttgc cacgccgtcg atgtttggct    540
aaaacggtgc ataaaccagg tctcgctttg tttcctgatt ctttgtggag accagttggt    600
aacagtagtg ttaactggag cggtcttggc tgcaaaagtt tcgaatgctt gaaaggtaag    660
aaactgagcc gggattgtgt tggttgcttt gatctagcta ctagtcatga aaagatagg     720
tttgttaagg ttaatgggaa gactgatttc ctgatagatg atgttttgga tttaggcgat    780
gggaaaatcc gaataggatt cgatattagc agtggatcag gtacgtttgc tgctagaatg    840
gctgaaaaga atgtgaatat aatcagtaat acattgaata tagatgctcc tttcagcgaa    900
ttcatagctg cgagaggaat ttttccgttg ttcatgagtt tggatcagag attaccgttc    960
tacgacaatg ttttcgatct catacatgca tctaacggat tggatttagc ggttagtaat   1020
aaacccgaga gctggagtt cttgatgttt gatcttgatc ggatcttgaa acccggtgga   1080
ttgttctggt tagacaattt ctattgcggt aacgatgaga agaagagagt tcttacgcgt   1140
ttgatagaga ggtttgggta taagaagttg aaatggggtg ttggagagaa aactgatgct   1200
gaggttttc tctcggctgt tctgcaaaag cctgcccgga tttga                    1245

<210> SEQ ID NO 2
<211> LENGTH: 414
<212> TYPE: PRT
<213> ORGANISM: Arabidopsis thaliana L. Heynh.

<400> SEQUENCE: 2

Met Gly Ser Val Ser Leu Lys Ile Gly Asp Gly Thr Ala Arg Phe Lys
1               5                   10                  15

Arg Ser Thr Leu Phe Ser Ser Ala Ile Asn Leu Leu Met Leu Phe Ser
            20                  25                  30

Ile Val Thr Thr Asn Leu Phe Ala Leu Tyr Ala Phe Ser Ser Arg Ser
        35                  40                  45

Gln Ser His Thr Pro His Pro Leu His Ser Asn Asn Val Ser Leu Val
    50                  55                  60

Ser Gln His Leu Ser Leu Ile Leu Arg Glu Ile Asp Ser Ser His His
65                  70                  75                  80

Thr Leu Thr Gln Met Glu Lys Gln Ile Ile Gly Tyr Glu Ser Leu Asp
                85                  90                  95

Leu Ser Gln Gln Glu Val Pro Gln Glu Leu Lys Leu Phe Leu Gln Gln
            100                 105                 110

His Gln Leu Pro Leu Gly Lys Asp Ser Arg Thr Gly Ile Thr Gln Met
        115                 120                 125
```

-continued

Val Ala Ser Val Gly His Ser Cys Glu Met Ser Leu Asp Leu Leu Ser
            130                 135                 140

Gln Tyr Met Ser Tyr Asn Val Phe Glu Lys Cys Pro Asp Asp Trp Ser
145                 150                 155                 160

Leu Ala Gln Lys Leu Ile Leu Arg Ala Cys Glu Pro Leu Pro Arg Arg
                165                 170                 175

Arg Cys Leu Ala Lys Thr Val His Lys Pro Gly Leu Ala Leu Phe Pro
            180                 185                 190

Asp Ser Leu Trp Arg Pro Val Gly Asn Ser Ser Val Asn Trp Ser Gly
                195                 200                 205

Leu Gly Cys Lys Ser Phe Glu Cys Leu Lys Gly Lys Leu Ser Arg
210                 215                 220

Asp Cys Val Gly Cys Phe Asp Leu Ala Thr Ser His Glu Lys Asp Arg
225                 230                 235                 240

Phe Val Lys Val Asn Gly Lys Thr Asp Phe Leu Ile Asp Asp Val Leu
                245                 250                 255

Asp Leu Gly Asp Gly Lys Ile Arg Ile Gly Phe Asp Ile Ser Ser Gly
            260                 265                 270

Ser Gly Thr Phe Ala Ala Arg Met Ala Glu Lys Asn Val Asn Ile Ile
            275                 280                 285

Ser Asn Thr Leu Asn Ile Asp Ala Pro Phe Ser Glu Phe Ile Ala Ala
290                 295                 300

Arg Gly Ile Phe Pro Leu Phe Met Ser Leu Asp Gln Arg Leu Pro Phe
305                 310                 315                 320

Tyr Asp Asn Val Phe Asp Leu Ile His Ala Ser Asn Gly Leu Asp Leu
                325                 330                 335

Ala Val Ser Asn Lys Pro Glu Lys Leu Glu Phe Leu Met Phe Asp Leu
            340                 345                 350

Asp Arg Ile Leu Lys Pro Gly Gly Leu Phe Trp Leu Asp Asn Phe Tyr
            355                 360                 365

Cys Gly Asn Asp Glu Lys Lys Arg Val Leu Thr Arg Leu Ile Glu Arg
            370                 375                 380

Phe Gly Tyr Lys Lys Leu Lys Trp Val Val Gly Glu Lys Thr Asp Ala
385                 390                 395                 400

Glu Val Phe Leu Ser Ala Val Leu Gln Lys Pro Ala Arg Ile
                405                 410

<210> SEQ ID NO 3
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 3
acattctaca actacatcta gagg                                          24

<210> SEQ ID NO 4
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 4
cggccgcccc ggggatc                                                  17

US 9,862,961 B2

BIOMASS PRODUCTION INCREASING GENE AND TRANSGENIC PLANT USING SAME

CROSS-REFERENCE TO RELATED APPLICATIONS

This application is the U.S. national phase application filed under 35 U.S.C. §371 claiming benefit to International Patent Application No. PCT/KR2013/004186, filed on May 10, 2013, which is entitled to priority under 35 U.S.C. §119(a)-(d) to Korea application no. 10-2012-0061613, filed Jun. 8, 2012, each of which application is hereby incorporated herein by reference in its entirety.

TECHNICAL FIELD

The present disclosure relates to a gene for increasing production of biomass isolated from Arabidopsis thaliana, and a method of producing a transgenic plant using the same, etc.

BACKGROUND ART

As the era of high oil prices has arrived, the importance of plant biomass is being magnified as a source of bioenergy. A first generation biofuel production using a saccharification process of starch which is present in crops has caused a rise in agricultural commodity prices, food shortages, and a financial crisis, and thus the development of the related art is being eschewed. Whereas a study on a second generation biofuel production using lignocellulosic cellulose which is present in silver grass, switch grass, and poplar, which are inedible biomass crops, is vigorously in progress. However, the efforts to increase and continuously maintain plant biomass production may be required basically to produce a large amount of energy enough to substantially substitute for a fossil fuel. Accordingly, a study on the development of vascular tissues including a cambium which mainly affect a secondary growth and the growth control mechanism is required.

The vascular tissues of plants, as a moving path of materials which are necessary for the growth and development of plants including water and nutrients, have a distinguishing structure formed by each of the cells having a specific function. In an elongation, which is a primary growth, the vascular tissues of the stem are generated by an apical meristem which is present at the uppermost part, and include a procambium, primary phloem, and xylem. Cambium cells expanded in a fibrovascular tissue between the bundles for the secondary growth are formed over time, secondary phloem and xylem are developed in an opposite direction from the cambium cells as an initial cell, and thereby a closed ring-shaped structure is formed.

Various plant growth hormones become involved in the development of vascular tissues of the stem. Auxin and cytokinin which are closely related to the activity of overall meristematic tissues affect cell division of the cambium, and gibberellin and ethylene also become involved in activity of the cambium. Further, brassinosteroid controls the number or pattern of the vascular bundle, which is determined according to the auxin maxima generated by controlling the movement of auxin. In addition, specific genes are known for becoming involved in each tissue-specific formation. For example, ATHB8, CNA(ATHB15), PHB, PHV, and REV which belong to a HD-ZIP III gene group are all mainly expressed in the cambium of vascular tissues, and development directions of phloem and xylem, and differentiation of xylem are known to be controlled by the above-described genes in each of the vascular bundles. Further, KANADI which is another control factor controls expression of the above-described HD-ZIP III through miRNA165/166, and this is reported to control a formation of vascular tissues through interaction with auxin.

Although a study on this complex mutual control action is well performed, a case of changing an amount of biomass which may be actually produced through a modification of the related gene has not been reported. This means that a factor becoming involved in the development of the specific tissues has a limitation in increasing an amount of production of biomass.

However, Arabidopsis thaliana has a short first generation period of about 6 weeks from germination to the formation of the next seed, and mutants of Arabidopsis thaliana having various forms may be simply made using chemical materials. Further, the size of Arabidopsis thaliana is small enough to be raised in a glass container, and the size of the genome is small. Accordingly, Arabidopsis thaliana is a popular model organism in the study of plants. A plant height is about 30 cm, a flower bud is formed about 3 weeks after germination under long-day conditions, the first seed may be obtained in 5 to 6 weeks, and self-fertilization is possible as well as artificial crossing. The most noticeable characteristic is that Arabidopsis thaliana is a plant having the smallest genomic size in phanerogamous plants, the size of the genome is known to be $1 \times 10^8$ base pairs/haploid. The chromosome number is 2n=10, and a repeated sequence is small, either. A genetic map of which a title is restriction fragment length polymorphism (RELP) was completed by Howard Goodman, etc. of Massachusetts Institute of Technology (MIT), and a dielectric plan of "the Arabidopsis thaliana edition" was launched from 1990 under the aegis of the National Science Foundation (NSF). Accordingly, the present inventors attempted to find a new gene to increase the biomass production using Arabidopsis thaliana which has the above-described advantages.

DISCLOSURE

Technical Problem

In order to increase production of plant biomass which is a source of bioenergy, a gene for increasing activity of cambiums of plants was found by the present inventors, and a transgenic plant of which an amount of biomass production is increased becomes capable of being produced by using the gene. The present disclosure is completed based on the above description.

Accordingly, the present disclosure is directed to providing a composition for increasing production of plant biomass, which includes a base sequence encoding an amino acid sequence of SEQ ID NO: 2, and a transgenic plant which is transformed using the composition.

Further, the present disclosure is directed to providing a method including a step of transforming a plant using the composition.

Technical Solution

To address the issues described above, in an embodiment of the present disclosure, cross sections of stems were observed using a FOX (Full-length cDNA Over-eXpressing gene) hunting system in which each of about 12,000 units of Arabidopsis thaliana full-length cDNA is overexpressed, the individual of which activity of the cambium was increased was sorted, and overexpressed genes which are expected to affect a phenotype were isolated and identified. Then, these genes were proven to actually induce the phenotype through experiments, and various phenotypes related to biomass which are shown from overexpressing transformants of the corresponding genes were determined.

As a result, according to an aspect of the present disclosure, there is provided a composition for increasing production of plant biomass, including a base sequence encoding an amino acid sequence of SEQ ID NO: 2.

According to an exemplary embodiment of the present disclosure, the base sequence encoding an amino acid sequence of SEQ ID NO: 2 has a base sequence of SEQ ID NO: 1.

However, mutations in a base sequence may not lead to a change in proteins due to degeneracy of a codon. Accordingly, it is clear for those skilled in the art that the base sequences used in an embodiment of the present disclosure are not limited to the base sequences of SEQ ID NO: 1 described in an accompanying list of a sequence.

Further, a gene may be introduced using a recombinant vector for plant expression to obtain an effect of increasing biomass production. Accordingly, the present disclosure provides a composition for increasing production of plant biomass, including a recombinant vector for plant expression to which a base sequence encoding an amino acid sequence of SEQ ID NO: 2 is inserted. The recombinant vector for plant expression used in an embodiment of the present disclosure is not limited, and may include pCB302ES, pCXSN, pINDEX3, pBI121, pgR106, etc.

Further, according to another aspect of the present disclosure, there is provided a transgenic plant which is transformed using one of the compositions of an embodiment of the present disclosure. The plant used in an embodiment of the present disclosure is not limited, and may include *Arabidopsis thaliana*, tobacco, tomatoes, silver grass, switch grass, poplar, etc.

Further, according to still another aspect of the present disclosure, there is provided a method of increasing production of plant biomass, including a step of transforming a plant using one of the compositions of an embodiment of the present disclosure.

Advantageous Effects

The transgenic plant of which activity of a cambium is increased may be produced using a gene for increasing biomass production of an embodiment of the present disclosure, in other words, using a cambium activity control gene, ICA2 (at5g40830). Further, when producing a species of a grain having increased headings, a physical supporting force of a stem may be strengthened, and thereby a lodging problem due to an increased weight of the grain may be resolved.

DESCRIPTION OF DRAWINGS

In FIG. 3 (b), a red color means a first internode, an orange color means a second internode, a yellow color means a third internode, a green color means a fourth internode, and a navy blue color means a fifth internode;

BEST MODES OF THE PRESENT DISCLOSURE

Figure 1:
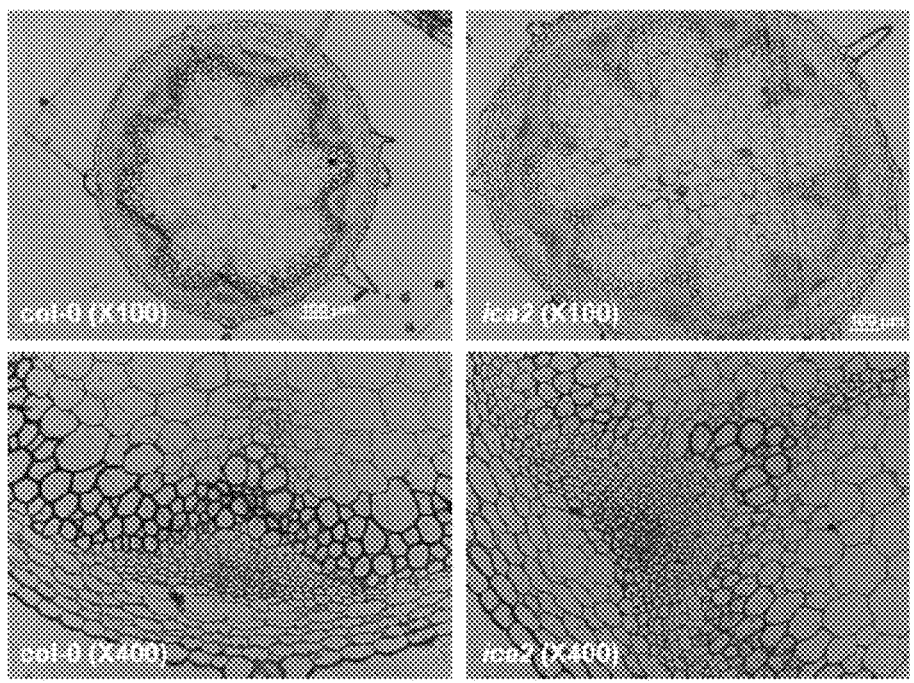
FIG. 1 is a view illustrating phenotypes in vascular tissues of ica2 and expression patterns of genes, and showing cross sections of stems (a), a comparison of thickness (b), and identification of overexpressed genes inducing the phenotypes of a wild type and ica2 (c)

Characteristics of a primary and secondary growth shown in the exterior of the stem and a morphological variation in vascular tissues of the interior of the stem were observed using a FOX (Full-length cDNA Over-eXpressing gene) hunting system in which each of about 12,000 units of *Arabidopsis thaliana* full-length cDNA is overexpressed. In particular, the individual of which cambium cell numbers are increased, which is a phenotype directly related to an increase of biomass was sorted. The sorted transgenic plant was determined to show a phenotype of all increased cell numbers and layer numbers of a procambium and have all increased vascular tissues such as xylem, phloem, or the like as compared to a wild type, and was called ica2 (Increased Cambial Activity2) (refer to FIG. 1a). This may be inferred as a result of increased activity of a cambium which has meristem characteristics capable of differentiating into other organs. In addition, thicknesses of all stems are also increased 30% or more as compared to a wild type, which may be expected to affect a biomass increase (refer to FIG. 1b).

First, an experiment of isolating and identifying overexpressed genes of ica2 was performed to find a gene mediating the phenotype shown in the stems. As a result, the sorted transformant was determined to has an overexpressed at5g40830 gene which is a methyltransferse, and the corresponding gene was called ICA2 (refer to FIG. 1c). To understand a role of an ICA2 gene in development of vascular tissues at a molecular level, a conventionally-reported expression pattern was analyzed and a candidate group of vascular tissue specific genes were sorted, and each expression level of each internode of stems of plants was observed. As a result, expressions of PXY, ATHB8, WOX4 (specific expression in a procambium), XCP2 (specific expression in xylem), and SUC2 (specific expression in phloem), which are candidate groups, were determined to increase in ica2 as compared to a wild type (refer to FIG. 2). When analyses of phenotypes and expression patterns are gathered together, phenotypes shown in stems are resulting from an expression control of a vascular bundle control gene.

To increase biomass per each individual plant, a length growth of a stem is important as well as an increase in stem thickness of a specific portion. Further, a promotion of the length growth of the stem is related to a thickness increase in a wide range based on a major axis of the stem. Further, in *Arabidopsis thaliana*, a secondary growth starts from a bottom side after a stem is formed and a primary growth is over, a lower side in which an axillary meristem is generated may accumulate more biomass than an upper side in which seeds grow. As a result of comparing and observing a stem growth of ica2 and a wild type according to this basis, an internode part capable of generating an axillary meristem in a stem of ica2 became twice or more longer than that of a wild type (refer to FIG. 3a). A difference in development of stems may be determined from the number of internodes. A length of each internode of ica2 is similar to that of the wild type, but the number of internodes of ica2 was increased 1.9 times as compared to the wild type (refer to FIG. 3b, c). Since the number of internodes is proportional to the number of the axillary meristem, the increased number of internodes suggests that an amount of biomass which may be obtained from one individual was increased. Accordingly, the ICA2 (at5g40830) gene may be determined again to become involved in a biomass increase. The number of internodes is closely related to the flowering, and thus it is known that as the flowering is delayed, the number of internodes increases. The flowering was delayed about 4 days as compared to the wild type under long-day conditions, and 4 leaves of ica2 were observed to increase as a result of the increased vegetative growth steps (refer to FIG. 3d, e). To understand phenotypes with respect to the flowering time at a molecular level, an expression of FT which is known as an important integrate factor in the flowering was determined, and as a result, a FT expression was maintained at a lower concentration in ica2 than in the wild type (refer to FIG. 3f). Accordingly, a probability of a correlation between the ICA2 gene and a flowering control gene may be inferred from the above description.

Figure 4:
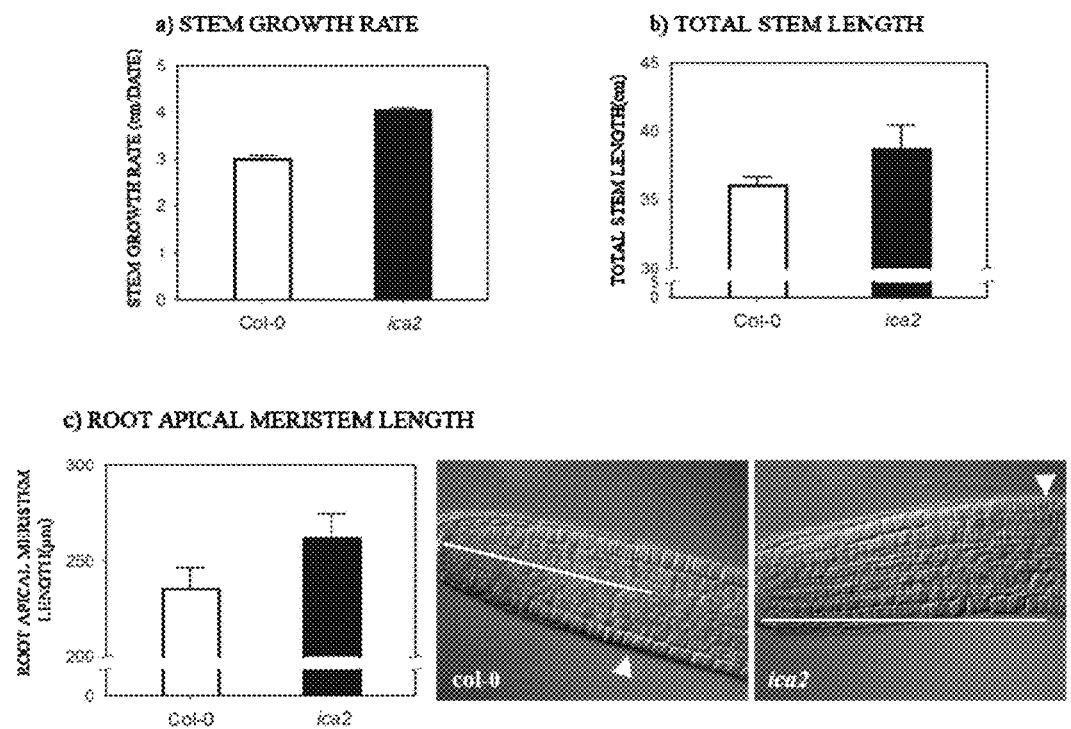
FIG. 4 illustrates a result of an experiment observing a growth rate (a) and total length (b) from a stem, and a length of meristem section (c) from a root, to determine a probability for controlling apical meristem activity.

Further, when the length of the stem was circadian measured and a growth rate for a day was determined, the growth rate of ica2 was shown to be 1.3 times or more faster (refer to FIG. 4a), and thus total length growth may be determined to be affected due to the fast growth of the stem even though the flowering is late. When a total length of ica2 was observed, the total length of ica2 was determined to slightly increase as compared to the wild type (refer to FIG. 4b). When these phenotypes of the stem are put together, the ICA2 gene is considered to serve to generally increase an amount of biomass by controlling a lateral meristem, controlling apical meristem activity of the stem as well as a thickness which is an index of the secondary growth, and becoming involved in a length growth. The increased length of the apical meristem accounting for the root of ica2 may be proof supporting this hypothesis (refer to FIG. 4c).

Experiments for determining a molecular control mechanism of ICA2 with respect to the above-described phenotypes were performed. In order to verify that this gene gets involved in development of the vascular bundle, first of all, expression patterns per development periods and organs of the ICA2 gene were analyzed. As a result, an expression was determined in vascular tissues of a cotyledon and root (refer to FIG. 5). Further, in that this gene is expressed in an endosome such as a cytoplasm and endoplasmic reticulum in cells (refer to FIG. 6), the object for a methylation is likely to be proteins or secondary metabolites other than DNA or RNA. When a microarray analysis which is mainly used for transcriptome analysis is used, gene groups which are directly and indirectly affected by the ICA2 gene may be checked, and thus it is expected to help understand a maintenance and differentiation mechanism of the lateral meristem.

As described above, according to an embodiment of the present disclosure, it is obvious that the primary and secondary growths of plants are all increased, and thereby leading to an increase in biomass per one individual. Accordingly, the ICA2 gene of an embodiment of the present disclosure and ica2 which is the transgenic plant thereof are expected to be used in various applications for biomass production.

Hereinafter, exemplary embodiments of the present disclosure will be described in detail. However, the following exemplary embodiments of the present disclosure are merely provided for the purpose of understanding the present disclosure, and the present disclosure is not limited to the embodiments disclosed below.

EXAMPLE

Example 1. Selection of Mutant Increased Procambium Activity from *Arabidopsis thaliana* and Vascular Tissues Phenotype Analysis (1) Observation of Cross Section of Stem Seeds of about 12,000 transgenic plants made from Col-0, which is a wild type of *Arabidopsis thaliana*, using RAFL (RIKEN *Arabidopsis* full-length cDNA) were obtained from RIKEN. The plants were grown in a greenhouse in which a temperature was controlled to about 23° C. under long-day conditions (16 hours day/8 hours night, circadian period). Even when the transgenic plants are grown on the same days, the transgenic plants have different growth cycles from each other. Thus, to observe the plants of the same period, when one silique is produced, the lowermost part of a stem was cut to about 5 mm in a state in which the stem was immersed in 3% glutaraldehyde and 0.1 M sodium phosphate buffer (pH 7.2), and collected. After being immersed in the solution, vacuumed for 10 minutes, and reacted for 3 hours at 4° C. to fix the sample, and general resin embedding was performed thereon. (After shaking the sample with a rocker at room temperature and cleaning the sample with 0.1 M sodium phosphate buffer (pH 7.2) 2 times for 20 minutes, a dehydration reaction was performed using 30% acetone that was increased 10% every interval of 10 minutes to 100%. After acetone was changed to a new second 100% acetone and a reaction was performed for 8 to 9 hours, the sample was processed once more using an additional new 100% acetone for 10 minutes. After a ratio between a resin and acetone was changed to 1:3, 1:2, 1:1, and 2:1 by increasing an amount of the resin in an interval of 1 hour, a process in which 100% resin was substituted in an interval of 2 hours and vacuumed for 10 minutes was repeated a total of 3 times. The resin sample was prepared by solidifying the resin in an oven at 65° C. for 24 to 48 hours using an embedding mold.) After the resin sample was (refined to have a shape of a square or trapezoid such that entire tissues are exposed) cut to a 2 μm section (using a glass knife or diamond knife), the sample was dyed using 0.05% toluidine blue, and a cross section thereof was observed. Accordingly, the individual of which the number of cells and layers in a procambium were increased as compared to a wild type was sorted out, and a thickness of a cross section of a stem was measured using a microscope.

(2) Identification of Overexpressed Gene of ica2

In order to find the corresponding foreign gene which shows various phenotypes in vascular tissues of ica2, genomic DNA was extracted from ica2. After a leaf was rapidly frozen using liquid nitrogen, the frozen leaf was ground up using a stainless bead, added to 250 µl of an extracted solution including 0.1 M Tris-Cl, 0.05 M EDTA, 0.5 M NaCl, and 1.25% SDS (pH 8.0), and then processed at 65° C. for 15 minutes. A phenol:chloroform:isoamylalcohol (25:24:1) solution having the same volume (250 µl) was further added, and the mixed solution was shaken up and down for 5 to 10 minutes to be well mixed. After centrifugation at 13,000 rpm and 4° C. for 10 minutes, a supernatant liquid was moved to a new tube, isopropanol having the same volume as the liquid was added thereto, the mixed solution was mixed by shaking up and down for about 10 times, and then centrifugation at 13,000 rpm for 1 minute was performed again. After removing a supernatant liquid, a DNA pellet was cleaned using 70% ethanol, a resuspension process was performed using 30 µl of water, and genomic DNA was extracted. A PCR was performed on the genomic DNA using a primer specific to a vector base sequence, which is used to transform plants (GS4, sequence number 3,5'-ACATTCTACAACTACATCTAGAGG-3'; GS6, sequence number 4,5'-CGGCCGCCCCGGGGATC-3'). 1% agarose gel electrophoresis was performed on an amplified fragment, the fragment was dyed with EtBr, a size thereof was determined, and then the DNA was extracted from the gel for determining of a cDNA base sequence of ICA2 (at5g40830) gene through sequencing. To verify expression of this gene in the transgenic plant, qRT-PCR was performed using RNAs extracted from the stem.

(3) Analysis of Expression of Each Tissue Specific-Marking Gene

To molecularly verify phenotypes in which all vascular tissues including the procambium are increased, after RNAs were extracted from the 1 cm of the upper side of the uppermost internode of a stem bearing 6 siliques using a Trizol reagent, cDNA was synthesized using a reverse transcription-polymerase chain reaction (RT-PCR), and then qRT-PCR was performed using primers specific to PXY, ATHB8, WOX4, XCP2, SUC2, and UBQ1, which is a control gene. These genes are known as a gene specifically expressed in vascular tissues and functioning, and PXY, ATHB8, and WOX4 correspond to the procambium, XCP2 corresponds to xylem, SUC2 corresponds to phloem.

Figure 2:
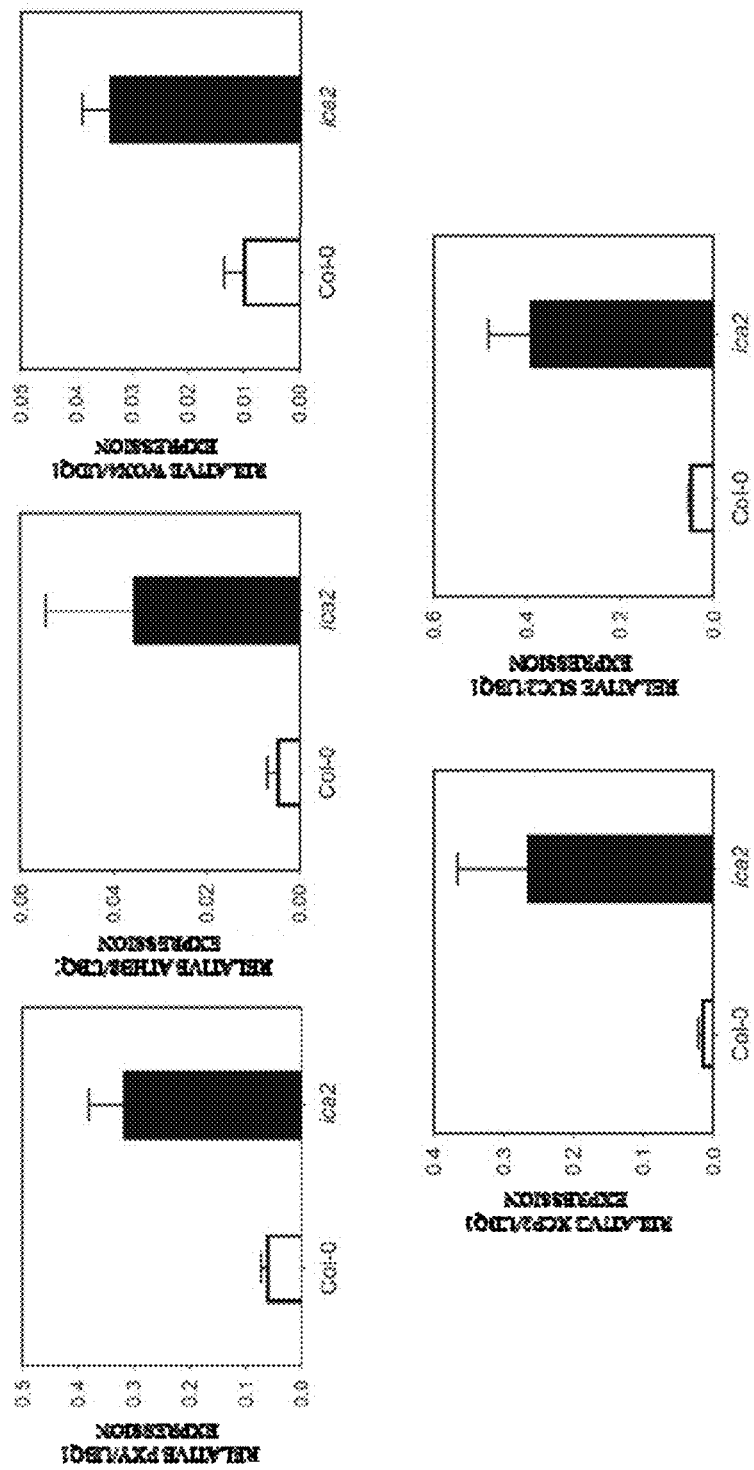
FIG. 2 illustrates a result of determining expression patterns of genes which are specifically expressed in vascular tissues (from left upper side, PXY/UBQ1, ATHB8/UBQ1, WOX4/UBQ1, XCP2/UBQ1, and SUC2/UBQ1)

The cross section of the stem observed using the above-described method was shown in FIG. 1a. The thickness of the stem measured using the above-described method was shown in FIG. 1b, an identified ICA2 (at5g40830) gene was verified to be overexpressed in the transgenic plant as compared to the wild type, which was shown in FIG. 1c. Further, as shown in FIG. 2, expression of the genes known for being specifically expressed in vascular tissues respectively and functioning was determined to increase in ica2 by the above-described method.

Example 2. Investigation of Various Traits Related to Biomass and Flowering (1) Stem Length Measurement After the wild type and ica2 were grown in a 0.5×B5 culture medium for 7 days and planted in a soil, the number of internodes was determined when each stem had grown to a size of about 5 cm, and thereafter, a stem length was measured every day for each internode during 7 to 10 days. When there was no change in the length for 3 days or more, the stem was assumed not to further grow, and the length of the total internode was calculated through the lengths of each internode and shown in FIGS. 3a, b, and c.

Figure 3:
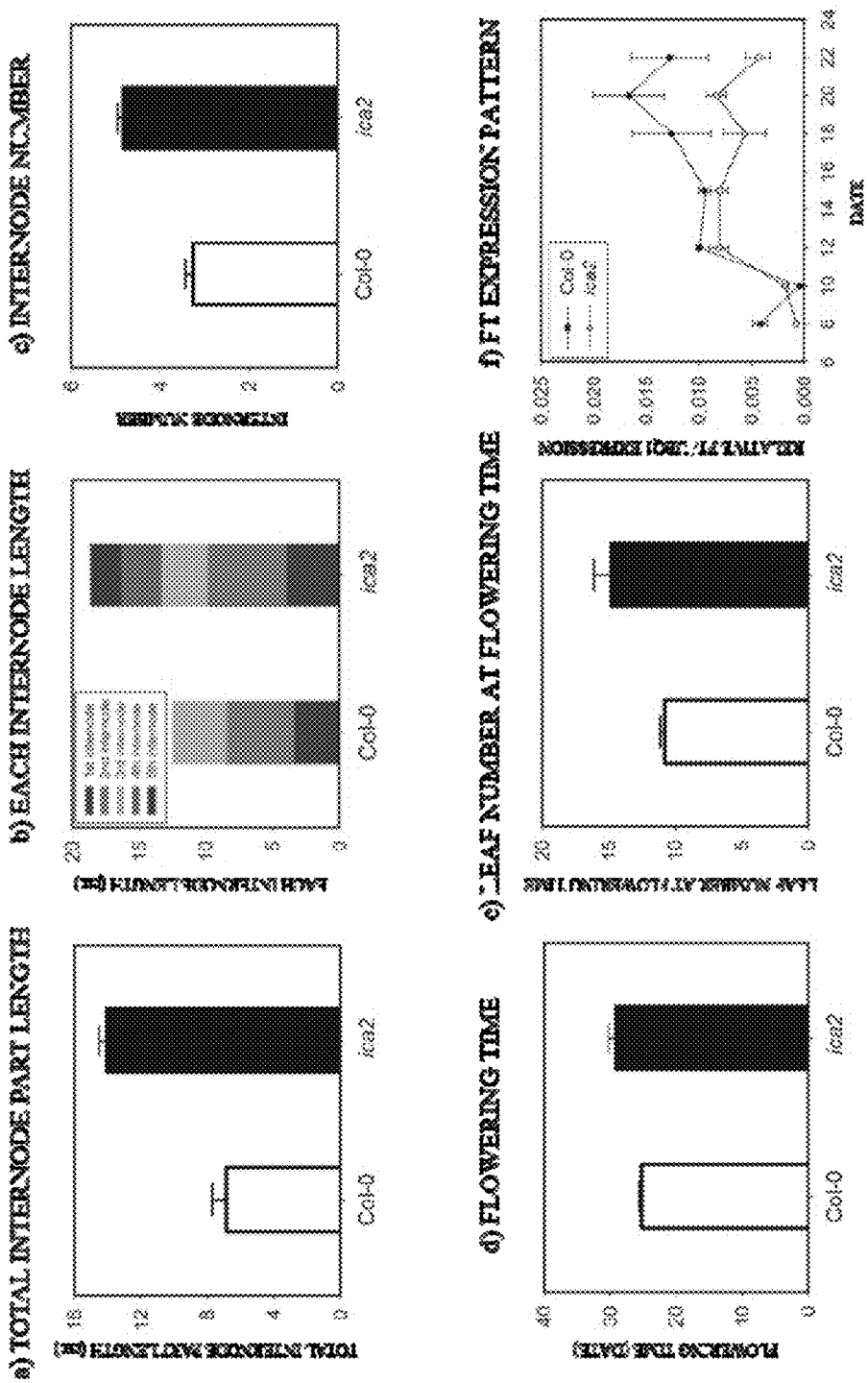
FIG. 3 is a view illustrating an analysis of other phenotypes, and representing an overall or individual internodal length (a and b), change of node numbers (c), delayed flowering time (d and e) and expression change (f) of FT which is a representative flowering control integrator, capable of supporting the above (a, b, c, d, and e).

According to FIGS. 3a, b, and c, while the length of total internode of ica2 is the same as that of the wild type, in ica2, the number of internodes was increased.

(2) Flowering Time Determination 7 days after placing the wild type and ica2 in a culture medium, the plants were planted in a soil, after the stem was formed, and time was measured until the length of the stem reached about 1 cm, at which time, the number of leaves was determined and shown in FIGS. 3d and e. Further, to molecularly understand phenotypes with respect to flowering time, RNAs were extracted at a part of the plant above the ground surface in an interval of 2 to 3 days from the eighth day after seeding, at the same time period (day conditions between 14 to 16 hours), and thereby expression of FT which is known as a representative flowering control integrator was determined through qRT-PCR, of which the result was shown in FIG. 3f. According to FIGS. 3d, e, and f, the flowering time of ica2 may be determined to be delayed and FT expression of ica2 may be determined to be decreased.

Example 3. Analysis for Control of Activity of Apical Meristem

Whether or not ica2 affects control of apical meristem activity as well as lateral meristem activity, analysis for control of activity of apical meristem was performed.

(1) Apical Meristem Activity of Stem

Total length was measured with respect to the wild type and stems of the transgenic plants according to the method of Example 2 (1), and the length of the stem grown in a day was calculated based on the above description and marked with a growth rate. According to FIG. 4, the growth rate of the stem of the transgenic plant may be determined to be faster than that of the wild type (a), which indicates that a total length of the stem is also increased.

Through the above-described experiments, a probability that an ICA2 (at5g40830) gene found by an embodiment of the present disclosure becomes involved in control of activity of an apical meristem of the stem may be inferred.

(2) Apical Meristem Activity of Root

To verify a probability that the at5g40830 gene found by an embodiment of the present disclosure becomes involved in control of activity of the apical meristem, a length of meristem zone of the root, another apical meristem, was measured. The plant was stood up and grown in a 0.5×MS culture medium (1.5% agar) such that the root is grown erectly, 5 days after germination, (6 days after planting) the plant was collected, immersed in 1 ml of 0.24 N HCl (containing 20% methanol), and then processed in a heat block at 57° C. for 15 minutes. Then, the solution was removed, and the plant was reacted with 7% NaOH (60% ethanol) at room temperature. Ethanol was substituted with 40%, 20%, and 10% ethanol in an interval of 5 minutes through a rehydration process, and the plant was reacted with a 5% ethanol and 25% glycerol solution for 15 minutes. Thereafter, the plant was lined up on a slide glass, processed with 50% glycerol, covered with a cover glass without generating air bubbles, and observed using a microscope. In the root, an elongation zone starts from the part in which cells are small and cells are rapidly elongated twice or more in a meristemic zone. The length or the number of cells of from a quiescent centre to a last cell of the meristemic zone may represent activity of the meristem. FIG. 4c shows photographs of phenotypes of the wild type and ica2 in the root apical meristem, and a digitized graph thereof. Accordingly, even the apical meristem of the transgenic plant found using the method of an embodiment of the present disclosure is obviously affected.

Example 4. Determination of Spatio-Temporal Expression Aspect of At5G40830 RNA To observe an RNA expression aspect of ICA2, a promoter of the gene was recombined with pCAMBIA1303 (copyright © Cambia, Australia) binary vectors. After the promoter was amplified through PCR using a primer which specifically inserted EcoRI to 5', and NcoI to 3' of the front part of 2167 bp of the ICA2 gene promoter, a plasmid pCAMBIA1303-promoterICA2-GUS was prepared such that the promoter is fused with GUS proteins and expressed. This was used to transform agrobacterium to be expressed in plants, and then *Arabidopsis thaliana* was transformed using a floral dip method. After the transformed plants obtain seeds, independent individuals growing in a 0.5×MS, 30 mg/L hygromycin culture medium were sorted, planted in a soil, grown, and obtained seeds respectively and placed in a culture medium with the same compositions. Here, some parts of the population in which a ratio between the phenotypes of survivors and the dead was 3:1 were planted in a soil and some parts were dyed, and thereby used for analyzing expression patterns. Expression of GUS proteins was observed using a method of observing a root after immersing the plant in a 50 mM NaPO$_4$ (pH 7.0), 1 mM X0Gluc, 5 mM K$_3$Fe(CN)$_6$, 5 mM K$_4$Fe(CN)$_6$, 0.2% triton X-100 solution and reacting at 37° C. for 12 hours, or was observed using a microscope after processing the plant using 100% ethanol and removing a chloroplast.

Figure 5:
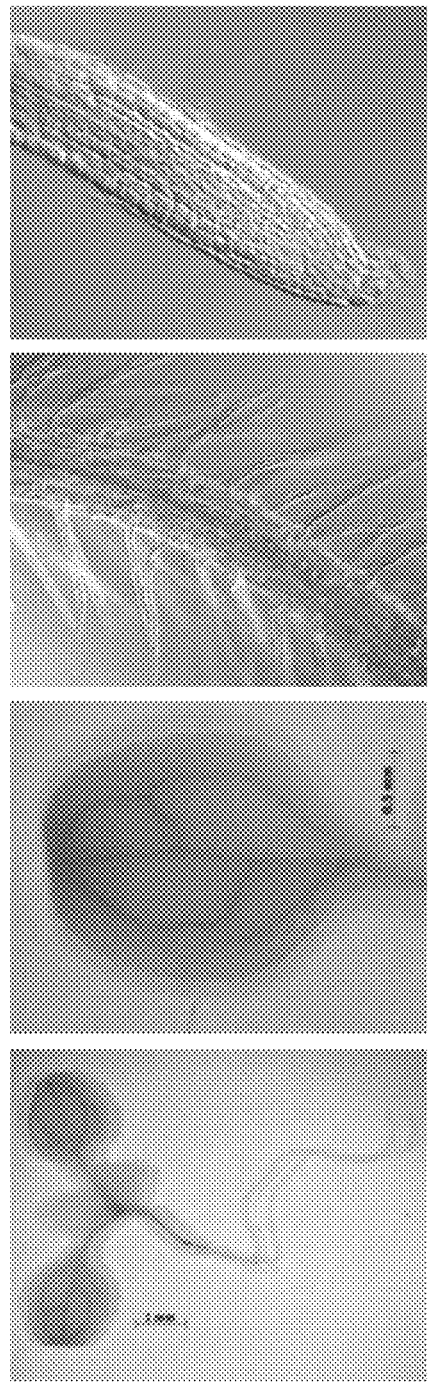
FIG. 5 illustrates sites in which ICA2 RNA is expressed in an 11 day-old plant.
Figure 6:
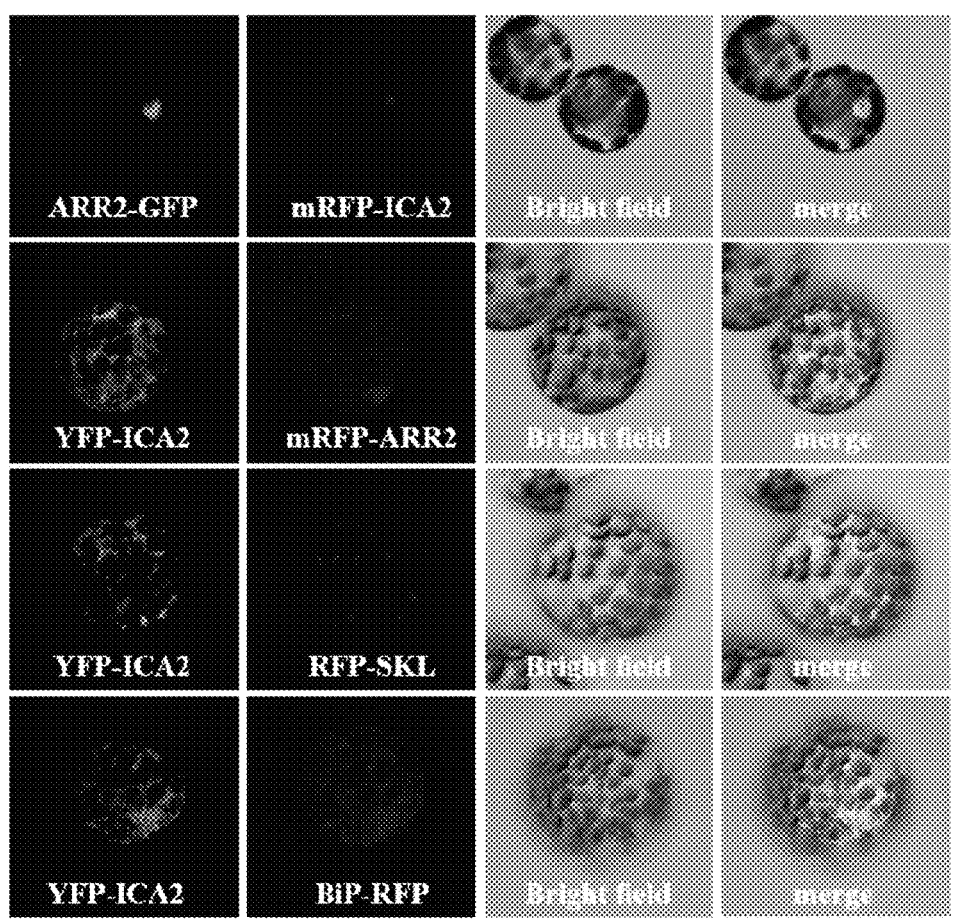
FIG. 6 illustrates a result of observing sites in which an ICA2 protein is expressed in one mesophyll cell protoplast with genes marking each minute organ.

According to FIG. 5, RNAs encoded by ICA2 are shown to be expressed in vascular tissues of a cotyledon and root. This is a result representing that phenotypes shown in vascular tissues of the transgenic plant proves that a precondition that ICA2 is expressed in vascular tissues and functions is valid.

Example 5. Determination of ICA2 Protein Expression Aspect in Cells

To express ICA2 proteins in a protoplast of a single mesophyll cell, the promoter was fused with GFP/mRFP/YFP which are fluorescence proteins and recombined with a plasmid for expression (35S promoter-ICA2-GFP/35S promoter-mRFP-ICA2/CsV promoter-YFP-ICA2). The recombinant plasmid was used after separating at a high concentration of 2 μg/μl using CsCl. To obtain a protoplast of a single mesophyll cell from *Arabidopsis thaliana*, after growing Col-0 which is a wild type for 3 to 4 weeks, leaves thereof were cut into small pieces, put into a 0.4 M mannitol, 20 mM KCL 20 mM MES, 1% cellulase, 0.25% macerozyme R10, 10 mM CaCl$_2$, 0.1% BSA solution, vacuumed for 30 minutes while blocking light with a foil, and then reacted at room temperature for 3 to 4 hours. Basically, ICA2 and marking genes which are expressed in each minute organ were combined in 2×10$^4$ cells, 40 μg of DNA was infected, and after 12 to 14 hours, expression in cells was observed using a confocal microscope and shown in FIG. 5. According to the result of the existing report, ICA2 proteins are known for having a signal targeted to a peroxisome, but in the result of expressing ICA2 proteins with SKL which is a marking gene for the corresponding minute organ and observing, ICA2 proteins were determined not to be expressed at the same site with SKL. Further, ICA2 proteins show different expression patterns from ARR2 which is one of the transcription factors which is expressed in a nucleus, but an expression site of BiP which is an endoplasmic reticlum marking gene definitely was determined to coincide with that of ICA2 proteins. Accordingly, a substrate in which ICA2 proteins work as a methyltransferse enzyme is likely to be proteins or the secondary metabolite present at the endoplasmic reticulum or cytoplasm rather than DNA or RNA positioned in a nucleus.

Consequently, ica2 in which an ICA2 gene is overexpressed shows a phenotype of increased biomass, and thus the present gene may be determined to increase applicability to use in applied crops.

Example 6. Analysis of Amino Acid Sequence of ICA2 Proteins

Figure 7:
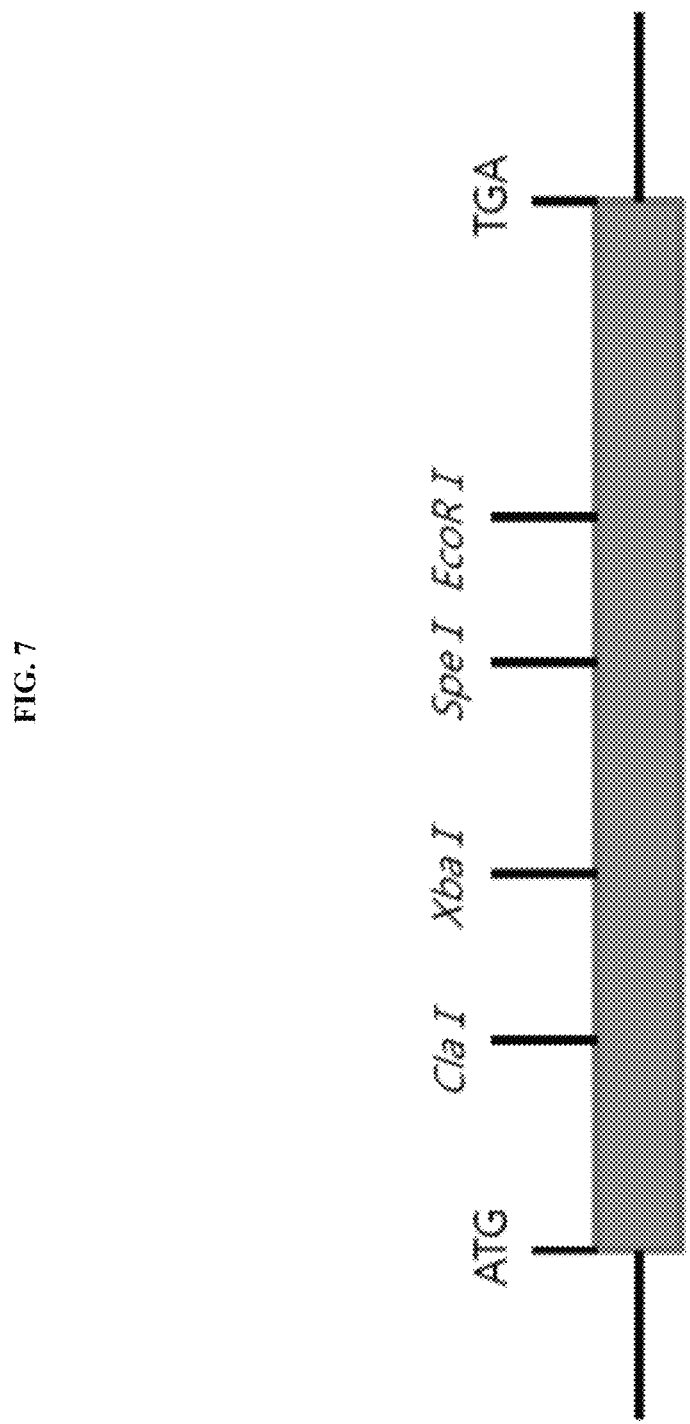
FIG. 7 illustrates sites of a restriction enzyme of ICA2 (at5g40830).

As a result of determining an amino acid sequence of a base sequence of an at5g40830/pGEM-T Easy vector including cDNA of ICA2 using an in silico translation tool of the BCM Search Launcher (http://searchlauncher.bcm.t-mc.edu), the base sequence was determined to have 414 amino acids which coincide with the database of TAIR (refer to FIG. 7), a molecular weight of about 46.5 kDa, an isoelectronic point (pI) value of 8.33. In the result searching for the amino acid sequence of ICA2 in the BLAST database (http://www.ncbi.nlm.nih.gov/BLAST), the amino acid sequence showed high homogeny with 3 methyltransferase genes.

In the result searching for a domain of which a function is known using the InterProScan program (http://www.ebi.ac.uk), the amino acid sequence was determined to have a methyltransferase 11 domain common with other methyltransferase, and thus proteins encoded by ICA2 was anticipated to have methyltransferase activity.

The above description about the present disclosure is merely for an example, and it will be apparent to those skilled in the art that various modifications can be made to the above-described exemplary embodiments of the present disclosure without departing from the spirit or scope of the disclosure. Thus, it should be understood that the embodiments described above are exemplary in every aspect and not restrictive.

INDUSTRIAL AVAILABILITY

The present disclosure may ultimately expand a source of the pulp and papermaking industry, and a source of bioethanol by increasing amounts of lignocellulosic cellulose. Further, the plant according to an embodiment of the present disclosure is expected to be used in the form of firewood or a pellet as a heating and power production source.

What is claimed is:

1. A transgenic plant comprising a recombinant vector, wherein the vector comprises the polynucleotide sequence of SEQ ID NO: 1 operably linked to a promoter, wherein the transgenic plant comprises increased cambium cell number and activity relative to the plant before transformation.

2. A method of increasing production of plant biomass, comprising a step of transforming a plant with a composition comprising a polynucleotide sequence encoding SEQ ID NO: 2.

3. The method of claim 2, wherein the polynucleotide sequence comprises the polynucleotide sequence of SEQ ID NO: 1.

4. The method of claim 2, wherein the transforming is conducted using a plant expression vector comprising the polynucleotide sequence.

5. The transgenic plant of claim 1, wherein the recombinant vector is pCB302ES, pCXSN, pINDEX3, pBI121, or pgR106.

6. The transgenic plant of claim 1, wherein the plant is *Arabidopsis thaliana*, tobacco, tomatoes, silver grass, switch grass, or poplar.

7. The method of claim 4, wherein the recombinant vector is pCB302ES, pCXSN, pINDEX3, pBI121, or pgR106.

* * * * *